(12) United States Patent
Kery et al.

(10) Patent No.: US 9,267,873 B2
(45) Date of Patent: Feb. 23, 2016

(54) MATERIAL SORTING SYSTEM AND METHOD OF SORTING MATERIAL

(75) Inventors: Robert Thomas Kery, New South Wales (AU); John Anton Gal, New South Wales (AU); Sung-Wei Chen, Singapore (SG)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 748 days.

(21) Appl. No.: 13/376,544

(22) PCT Filed: Mar. 30, 2011

(86) PCT No.: PCT/AU2011/000357
§ 371 (c)(1),
(2), (4) Date: May 21, 2012

(87) PCT Pub. No.: WO2012/129591
PCT Pub. Date: Oct. 4, 2012

(65) Prior Publication Data
US 2012/0247231 A1 Oct. 4, 2012

(51) Int. Cl.
*G01N 15/14* (2006.01)
*G01N 15/10* (2006.01)
*G01N 15/02* (2006.01)

(52) U.S. Cl.
CPC ........ *G01N 15/1031* (2013.01); *G01N 15/0266* (2013.01); *G01N 2015/0288* (2013.01); *G01N 2015/1006* (2013.01); *G01N 2015/1081* (2013.01)

(58) Field of Classification Search
CPC .......... B03C 7/00; B03C 7/003; B03C 7/006; B03C 7/12; G01N 15/0266; G01N 15/0288; G01N 15/1031; G01N 2015/1081; G01N 15/14; G01N 2015/149
USPC ............... 209/127.1, 127.3, 127.4, 128–130; 422/82.01
See application file for complete search history.

(56) References Cited

U.S. PATENT DOCUMENTS

| 1,297,159 A * | 3/1919 | Hedberg | 209/130 |
| 2,479,615 A * | 8/1949 | Guizzetti | 209/181 |

(Continued)

OTHER PUBLICATIONS

International Search Report and Written Opinion of PCT/AU2011/000357 dated May 18, 2011.

(Continued)

*Primary Examiner* — Joseph C Rodriguez
(74) *Attorney, Agent, or Firm* — Foley & Lardner LLP

(57) ABSTRACT

A material sorting system is disclosed. The system has an electrical charge device arranged to produce electrical charging conditions for substantially all particles of a material sample such that an electrical charge at least partially dependent on particle capacitance is imparted to one or more particles, and a particle delivery device operably connected to the electrical charge device and arranged to cause the one or more particles to move along a flowpath. The system also has a deflection device arranged to cause each particle to deviate from the flowpath an amount at least partially dependent on the electrical charge imparted to the particle, and a collection device in fluid communication with the deflection device. The collection device is arranged to collect the one or more particles at one or more locations corresponding to the amount of deviation of the one or more particles from the flowpath. A corresponding method is also disclosed. The material sorting system and method are suitable for sorting cells according to the level of cell differentiation.

31 Claims, 3 Drawing Sheets

(56) References Cited

U.S. PATENT DOCUMENTS

| | | | |
|---|---|---|---|
| 4,280,623 A * | 7/1981 | Legorreta | 209/3.1 |
| 5,483,469 A * | 1/1996 | Van den Engh et al. | 702/21 |
| 6,589,792 B1 * | 7/2003 | Malachowski | 436/63 |
| 6,861,265 B1 * | 3/2005 | den Engh | 436/177 |
| 7,691,636 B2 * | 4/2010 | Frazier et al. | 436/63 |
| 7,880,108 B2 * | 2/2011 | Schembri et al. | 209/128 |
| 7,880,109 B2 * | 2/2011 | Okuda et al. | 209/129 |
| 8,748,183 B2 * | 6/2014 | Durack et al. | 436/8 |
| 2007/0102634 A1 * | 5/2007 | Frey et al. | 250/288 |
| 2007/0145262 A1 * | 6/2007 | Tai et al. | 250/288 |
| 2010/0096547 A1 * | 4/2010 | Allmaier et al. | 250/283 |
| 2013/0256197 A1 * | 10/2013 | Katsumoto | 209/127.1 |
| 2014/0097129 A1 * | 4/2014 | Foster et al. | 209/579 |
| 2014/0193059 A1 * | 7/2014 | Muraki | 382/133 |
| 2014/0346047 A1 * | 11/2014 | Shinoda | 204/603 |

OTHER PUBLICATIONS

Davies, Cell Sorting by Flow Cytometry, *Flow Cytometry: Principles and Applications*, Humana Press Inc., Totawa, New Jersey (printed from Internet Sep. 30, 2011) http://www.facs.ethz.ch/docs/lit.

Sohn et al., Capacitance Cytometry: Mesuring Biological Cells One by One, *Proc Natl Acad Sci USA* (Sep. 26, 2000), 97(20):10687-10690.

Stephens et al., Light Microscopy Techniques for Live Cell Imaging, *Science* (Apr. 4, 2003), 300(5616):82-86.

Classical Electromagnetism, a branch of theoretical physics that studies consequences of the electromagnetic forces between electric charges and currents. (printed from internet Sep. 30, 2011), http://en.wikipedia.org/wiki/Classical_electromagnetism.

Capacitance, the ability of a capacitor to store energy in an electric field. (printed from internet Sep. 30, 2011), http://en.wikipedia.org/wiki/Capacitance.

Fluorescence-Activated Cell Sorter, is a machine that can rapidly separate the cells in a suspension on the basis of size and the color of their fluorescence. (printed from internet Sep. 30, 2011), http://users.rcn.com/jkimball.ma.ultranet/BiologyPages/F/FACS.html.

Lorentz Force, is the force on a point charge due to electromagnetic fields. (printed from internet Sep. 30, 2011), http://en.wikipedia.org/wiki/Lorentz_force.

Capacitance and Dielectrics, MIT Course Notes, Chapter 5 (printed from internet Sep. 30, 2011), http://web.mit.edu/8.02t/www/802TEAL3D/visualizations/coursenotes/modules/guide05.

Bonner et al., Fluorescence Activated Cell Sorting, *The Review of Scientific Instruments*, (Mar. 1972), 43(3):404-409.

Gossett et al., Label-free cell separation and sorting in microfluidic systems, *Anal Bioanal Chem* (2010) 397:3249-3267.

Niu et al., Real-time detection, control, and sorting of microfluidic droplets, Dept. of Physics and Institute of Nano Science and Technology, The Hong Kong University of Science and Technology, Clear Water Bay, Kowloon, Hong Kong, published online Oct. 3, 2007.

Prakash et al., A CMOS Capacitance Sensor that Monitors Cell Viability, *IEEE*, 2005, 1177-1180.

Schade-Kampmann et al., On-chip non-invasive and label-free cell discrimination by impedance spectroscopy, (printed from internet Oct. 12, 2010), http://onlinelibrary.wiley.com/doi/10.1111/j.1365-2184.2008.00548.x/abstract, (abstract).

Valero, et al., A miniaturized continuous dielectrophoretic cell sorter and its applications, *American Institute of Physics*, Biomicrofluidics 4, 022807 (2010).

Impedance Microflow Cytometry, Leister Process Technologies, Axetris Division—Schwarzenbergstrasse 12, CH-6056 Kaegiswil, Switzerland (printed from internet Oct. 12, 2010) http://www.facs.ethz.ch/partnership/Impediance_Flyer.

Blyszczuk, P., et al., "Embryonic Stem Cells Differentiate into Insulin-Producing Cells Without Selection of Nestin-Expressing Cells," International Journal of Developmental Biology, vol. 48, Issue 10, pp. 1095 1104 (Dec. 2004).

Flanagan, L.A., et al., "Unique Dielectric Properties Distinguish Stem Cells and Their Differentiated Progeny," Stem Cells, vol. 26, Issue 3, pp. 656-665 (Mar. 2008).

Jiang, P., et al., "Electrophysiological Properties of Human Induced Pluripotent Stem Cells," American Journal of Physiology—Cell Physiology, vol. 298, No. 3, pp. 486-495 (Mar. 1, 2010).

Park, C.H., et al., "In Vitro and In Vivo Analyses of Human Embryonic Stem Cell-Derived Dopamine Neurons," Journal of Neurochemistry, vol. 92, Issue 5, pp. 1265-1276, (Mar. 2005).

Pethig, R., et al., "Dielectrophoresis—A Review of Applications for Stem Cell Research," Journal of Biomedicine and Biotechnology, vol. 2010, pp. 1-7 (2010).

Xu, R., et al., "Functional Analysis of Neuron-like Cells Differentiated from Neural Stem Cells Derived from Bone Marrow Stroma Cells In Vitro," Cellular and Molecular Neurobiology, vol. 28, Issue 4, pp. 545-558 (Sep. 28, 2007).

\* cited by examiner

MATERIAL SORTING SYSTEM AND METHOD OF SORTING MATERIAL

CROSS-REFERENCE TO RELATED APPLICATION

This application is a U.S. national stage filing under 35 U.S.C. §371 of International Application No. PCT/AU2011/000357 filed on Mar. 30, 2011 entitled "Material Sorting System and Method of Sorting Material," the disclosure of which is incorporated by reference in its entirety.

BACKGROUND

Materials such as cells can be sorted by detecting differences between the cells and selectively sorting the cells according to the differences. Some such sorting techniques require that cells are modified by attachment of a suitable marker, with the marker being subsequently used to detect the differences and sort the cells.

This type of sorting system tends to suffer from low throughput, low yields and cell damage among others.

SUMMARY

By way of non-limiting examples, embodiments are now disclosed.

In at least one embodiment, a cell sorting system is provided. The cell sorting system has an electrical charge device arranged to produce electrical charging conditions for substantially all cells of a sample of cells such that an electrical charge at least partially dependent on cell capacitance is imparted to one or more cells of the sample of cells according to the cell characteristic. The system has a cell delivery device operatively connected to the electrical charge device and arranged to cause the cells to move along a flowpath, and a deflection device arranged to cause the cells to deviate from the flowpath an amount at least partially dependent on the electrical charge imparted to the cell. The system also includes a collection device in fluid communication with the deflection device, the collection device collecting the cells at one or more locations corresponding to the amount of deviation of the cells from the flowpath.

In at least one embodiment, a method of sorting cells is provided. The method involves providing a sample of cells, and producing electrical charging conditions for substantially all cells of the sample of cells such that an electrical charge at least partially dependent on capacitance is imparted to the cells. The cells move along a flowpath, and are caused to deviate from the flowpath by an amount at least partially dependent on the electrical charge imparted to the cell. The cells are then collected at one or more locations corresponding to the amount of deviation of the cells from the flowpath.

In at least one embodiment, a method of isolating target cells from a sample of cells is provided. The cells have at least one cell characteristic associated with a target cell capacitance. The method involves providing a sample of cells, and producing electrical charging conditions for substantially all cells of the sample of cells such that an electrical charge at least partially dependent on cell capacitance is imparted to the cells. The cells move along a flowpath, and are caused to deviate from the flowpath an amount at least partially dependent on the electrical charge imparted to the cell. The target cells having the at least one target cell capacitance are then collected at a location corresponding to the amount of deviation of the target cells from the flowpath.

In at least one embodiment, a material sorting system is provided. The system has an electrical charge device arranged to produce electrical charging conditions for substantially all particles of a material sample such that an electrical charge at least partially dependent on particle capacitance is imparted to the particles. The system also has a particle delivery device operably connected to the electrical charge device and arranged to cause the particles to move along a flowpath, and a deflection device arranged to cause each particle to deviate from the flowpath an amount at least partially dependent on the electrical charge imparted to the particle. A collection device in fluid communication with the deflection device collects the particles at one or more locations corresponding to the amount of deviation of the particles from the flowpath.

In at least one embodiment, a method of sorting material is provided. The method involves providing a sample of material particles, and producing electrical charging conditions for substantially all particles such that an electrical charge at least partially dependent on particle capacitance is imparted to the particles. The method also involves causing the particles to move along a flowpath, and causing each particle to deviate from the flowpath an amount at least partially dependent on the electrical charge imparted to the particle. Particles are collected at one or more locations corresponding to the amount of deviation of the particles from the flowpath.

In at least one embodiment, a method of measuring capacitance of one or more particles is provided. The method involves providing one or more particles, producing electrical charging conditions for the particles such that an electrical charge at least partially dependent on capacitance of the particles is imparted to the particles. The method also involves causing the particles to move along a flowpath, and causing each particle to deviate from the flowpath an amount at least partially dependent on the electrical charge imparted to the particle. The particles are collected at one or more locations corresponding to the amount of deviation of the particles from the flowpath, with each of the locations corresponding to a capacitance amount.

DETAILED DESCRIPTION

Figure 1:
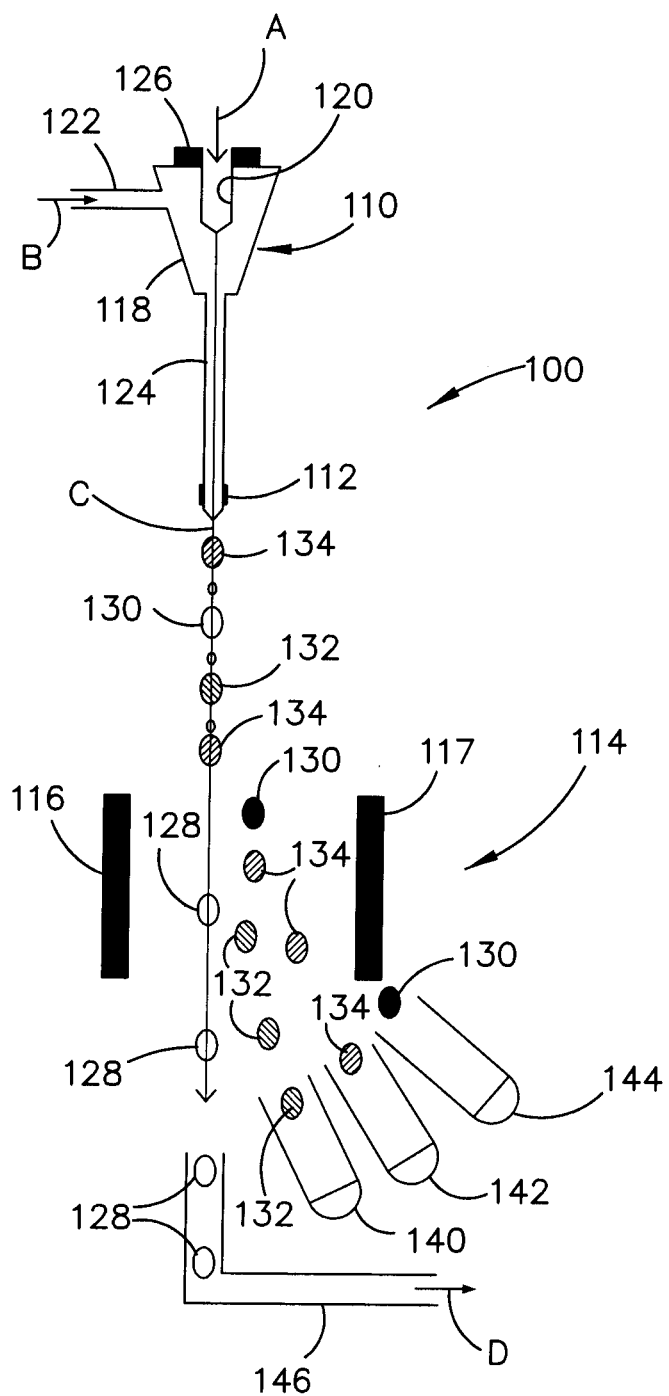
FIG. 1 is a diagrammatic representation of an example of a cell sorting system.

The following embodiments are described in relation to a sorting system and method wherein the material to be sorted includes cells having different characteristics, with the desire being to separate the cells according to one or more of the characteristics. However, it will be understood that sorting systems and methods for sorting material other than cells, such as particles according to one or more characteristics of the particles are also envisaged.

The sorting system is arranged to sort material using the electrical capacitance of items in the material when the electrical capacitance is at least partially dependent on at least one characteristic. For example, the electrical capacitance of a cell such as a stem cell is at least partially or completely dependent on the level of differentiation of the stem cell such that an increasing level of differentiation corresponds to increasing capacitance. Having regard to this relationship, it is possible to sort variably differentiated cells by exposing the cells to common charging conditions. In this way, the cells acquire a charge at least partially dependent on their respective capacitance, and subsequently passing the charged cells through a deflection device responsive to the electrical charge causes the cells to experience a variable force which results in a varying deviation from an initial flowpath. Since the amount of deviation is dependent on the charge, which in turn is dependent on the capacitance, the extent of deviation is indicative of cell differentiation. The separated cell streams are then collected separately at locations corresponding to the respective deviations.

However, it will be understood that the cells, or other material, may be separated according to any other characteristic wherein the capacitance is at least partially dependent on the characteristic.

For example, other capacitively differentiated bio-related molecules, such as micelles, double layer lipids (bilayer lipids), may be separated, or any particle having two concentric surfaces with charge differences, such as microspheres with different interior electrolytes.

In addition, characteristics other than level of cell differentiation are envisaged. For example, a desired separation characteristic dependent on capacitance might include cell cycle stage (related though distinct from cell differentiation), growth rate, cell damage/viability, cell membrane porosity (since a porous membrane will leak or admit ions), and cell ion content, such as cells with high ion transport channels and/or ion passage and usage.

Other non-bio related particles may also be sorted, for example particles wherein the particle capacitance is related to the size of the shell. With this type of particle, the particle resonant frequency is also related to the size of the shell. By sorting particles according to a specific range of characteristics which are capacitance related, particles of specific size and/or having specific resonant frequencies can be sorted. For example, with the present system and method it is possible to isolate gold nano-shells for plasmonic photo-thermal therapy that require a narrow range of resonant frequencies.

An example sorting system 100 for sorting cells is shown in FIG. 1. The system 100 is described herein in relation to separation of variably differentiated stem cells, although it will be understood that other cell types, or other particles, having capacitance amounts at least partially dependent on a characteristic desired to form the basis of sorting are envisaged.

The system 100 includes a cell delivery device 110 for receiving and producing a collimated stream of cells moving along a flowpath C, an electrical charge device 112 for producing common charging conditions for the cells moving along the flowpath C, and a deflection device shown in this example as two components, spaced deflection plates 116, 117, arranged to produce a common deflection electric field sufficient to cause each cell to deviate froth the flowpath C according to the amount of charge carried by the cell.

The cell delivery device 110 includes a cell sample inlet 120 for receiving a sample of cells desired to be sorted according to one or more characteristic, as indicated by arrow A, and a sheath fluid inlet 122 arranged to receive sheath fluid, as indicated by arrow B. In this example, the sheath fluid is pressurized and comprises saline solution, or other appropriate cell sorting media.

In some embodiments, a sheath pressure of 12.5 psi is used. This pressure can generate approx 27000 drops/sec and a flow velocity of 10 m/sec. In other embodiments, a pressure of 60 psi generating 100,000 drops per sec is used. However, it will be understood that any suitable pressure is envisaged.

The cell sample and sheath solution combine in a cell sample receptacle 118 and pass into an elongate collimator 124 which defines the flowpath C. The sheath fluid serves to assist in collimating the cell sample into a narrow linear stream flowing rapidly through the collimator 124, and pressurization of the sheath fluid serves to increase the fluid flow rate through the cell delivery device 110. In some embodiments, the desired linear stream is a substantially single file stream of droplets.

The cell delivery device 110 also includes a separation device arranged to minimize the likelihood of the cells sticking together and encourage the cells to separate from each other as the cell stream exits the collimator 124 by causing the cells to vibrate. In this example, the separation device comprises a piezo-electric transducer 126 that vibrates in response to an electric current and thereby causes at least part of the cell delivery device 110 to vibrate. In some embodiments, cells and sheath fluid are urged to move from a lower end of the cell sample receptacle 118 into the elongate collimator 124. By virtue of vibration imparted to the elongate collimator 124, droplets of regular size and spacing are created.

However, it will be understood that other vibration devices arranged to encourage the cells to vibrate are envisaged. For example, the cells may be caused to vibrate by sound waves.

As a result of the vibration imparted to the cell stream, droplets are produced. Some of the droplets have respective cells in them such and some of the droplets are without cells. By virtue of the separation device, typically each cell carrying droplet contains only one cell.

Prior to exiting the cell delivery device 110, the droplets are subjected to common charging conditions. In this example a common charging electric field is produced by an electrical charge device 112 by applying a substantially constant DC voltage to spaced charging plates. In this example, a voltage of about 100V is applied to the charging plates. However, it will be understood that any other suitable voltage is envisaged, such as 200V, calculated according to the calculations below in view of the relevant capacitances of the particles desired to be separated and the desired deflection amounts.

While the present embodiment includes an electrical charge device 112 in the form of 2 spaced charging plates to which a DC voltage is applied, it will be understood that other types of electrical charge device are envisaged. For example, the electrical charge device may comprise an electro-spray device or an aerosolization device.

Several types of droplets may exit the collimator 124 and in this example the droplets include uncharged droplets 128 that for any reason have not acquired a charge, droplets 130 that have acquired a charge but do not include a cell, droplets 132 that have acquired a charge and carry a respective first cell type, and droplets 134 that have acquired a charge and carry respective second cell types. In this example, the second cell type is more differentiated than the first cell type and, accordingly, the capacitance of the second cell type and therefore the charge acquired by the second cell type will be higher than the corresponding capacitance and charge acquired by the first cell type.

Since the sheath fluid is the same for all cells, the variation in capacitance of the droplets is substantially due only to the difference in capacitance of the cells.

Droplets without cells, that is droplets substantially entirely made up of sheath fluid, have a higher associated capacitance than droplets with cells and, accordingly, acquire a higher charge than the droplets 132, 134 with cells.

The deflection device 114 in this example produces an electric field extending in a direction substantially perpendicular to the flowpath C by applying a substantially constant DC voltage across the deflection plates 116, 117. In one example, the voltage is about 100V. However, it will be understood that any other suitable voltage is envisaged, such as 200V, calculated according to the calculations below in view of the relevant capacitances of the particles desired to be separated and the desired deflection amounts.

The droplets that have been caused to deviate from the flowpath C by the deflection device 114 are collected in first, second and third collection receptacles 140, 142, 144 respectively. The uncharged droplets 128 do not deviate from the flowpath C and continue to move along the flowpath C to be received in a recycle tube 146.

Although not shown in FIG. 1, material that is received in the recycle tube 146 may be recycled back to the cell sample inlet 120, as indicated by arrow D, whereupon the recycled cells are re-subjected to a charging voltage. In this way, efficiency of the system can be increased.

For a charged droplet, the deviation of the droplet from the flowpath C can be calculated as follows.

The charge on each droplet q is calculated as:

$$q = V_c C \quad (1)$$

where $V_c$ is the charging voltage produced by the electrical charge device 112, in this example across spaced charging plates, and C is the capacitance of the droplet.

The force on each droplet at the deflection device 114, in this example in response to a deflection voltage $V_d$ across the deflection plates 116, 117, is given by $$F = Eq \quad (2)$$

where E is the electric field across the deflection plates and q is the charge acquired by a droplet.

If d is the plate separation distance, then the electric field E across the deflection plates is given by:

$$E = \frac{V_d}{d} \quad (3)$$

Substituting (1) and (3) into (2) gives:

$$F = \frac{V_d V_c C}{d} \quad (4)$$

The deflection force F causes an acceleration a of a droplet having mass m in a direction transverse to the flowpath C towards one of the deflection plates 116, 117, as follows:

$$F = ma \quad (5)$$

Substituting (4) into (5) gives the acceleration a as:

$$a = \frac{V_d V_c C}{dm} \quad (6)$$

If the droplet is assumed to be travelling uniformly along the flowpath C at a velocity v prior to deflection by the charged deflection plates, then after a distance x in a direction parallel to the flowpath C the deflection y in a direction transverse to the flowpath C is calculated from:

$$x = vt \text{ and } y = \frac{1}{2}at^2 \quad (7)$$

and by eliminating t, we get:

$$y = \frac{1}{2}a\frac{x^2}{v^2} \quad (8)$$

Substituting (6) into (8) we get that the deflection y is given by:

$$y = \frac{V_d V_c C}{2dmv^2}x^2 \quad (9)$$

which represents a parabolic path for the droplet where the deflection is proportional to the capacitance of the droplet.

Each droplet containing a cell comprises a spherical cell enveloped by a thin shell of sheath solution.

The capacitance $C_d$ of the droplet containing a cell can be calculated as:

$$\frac{1}{C_d} = \frac{1}{C_s} + \frac{1}{C_c} \quad (10)$$

where $C_s$ is the capacitance of the sheath fluid around the cell and $C_c$ is the capacitance of the cell.

In equation (9), C represents the capacitance of the droplet, that is, $C_d$, and from (10) the deflection y in (9) can be written as:

$$y = \frac{V_d C_c C_s C_c}{2mdv^2(C_s + C_c)}x^2 \quad (11)$$

The deflection y is therefore dependent on the capacitance $C_d$ of the droplet.

Since the capacitance of the sheath fluid is significantly larger than that of the cell, the capacitance of each droplet is largely determined by the capacitance of each cell. Therefore for droplets containing cells, the deflection is approximately proportional to the capacitance of each cell. Given that the capacitance of differentiated cells is about twice that of undifferentiated cells the deflection of differentiated cells will be approximately double that of undifferentiated cells.

A droplet that does not contain a cell is effectively a sphere of sheath fluid and will have a capacitance that is significantly greater than droplets containing cells. As a consequence, a droplet that does not contain a cell will experience a greater deflection than droplets that contain a cell.

In the present example, the variably differentiated cells have a capacitance of the order of 15-30 pF. For example, human iPS and ES cells have a capacitance of the order of 15.4 pF, and undifferentiated BMSC-D-NSC cells have a capacitance of about 16.8 pF. Differentiated neuron-like cells from BMSC-D-NSC cells, however, have a capacitance of about 30.18 pF. Similarly, differentiated DA (dopamine) neurons with tyrosince hydroxylase have a capacitance of about 86.4 pF, which is about 5.5 times higher than the equivalent ES cells.

The above derivation can be used to determine the deflection in a typical case. It should be noted that these calculations are approximate only and there is considerable scope for tuning to optimize the throughput and yield.

For example, for a deflection voltage $V_d=100V$, charging voltage $V_c=100V$, droplets with associated cells of diameter 10 microns surrounded by a 1 micron sheath of aqueous medium, droplet mass $m=10^{-12}$ Kg, velocity of cells=10 m/sec, and deflection plate spacing d=3 cm, the deflection over a distance of 3 cm parallel to the flowpath C is of the order of 1.7 cm for undifferentiated cells, 3.4 cm for differentiated cells and 6.7 cm for droplets without cells.

There is considerable scope for tuning the system to provide optimal sorting and high yield by varying the charging and deflection voltages $V_c$, $V_d$, the separation d between the deflection plates, the length over which the deflection is applied, the speed of the droplets, the geometry of the plates, and the positioning of the collection receptacles.

Figure 2:
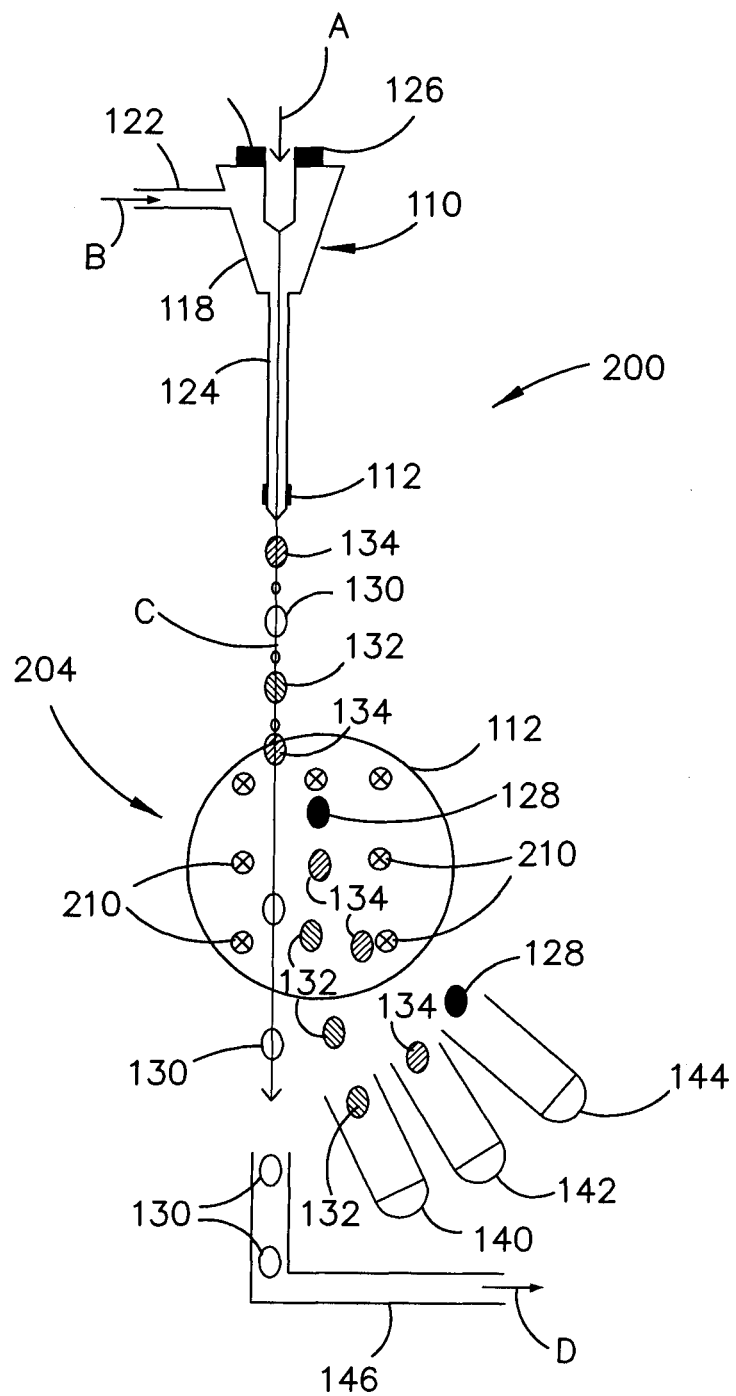
FIG. 2 is a diagrammatic representation of another example of a cell sorting system.

Another example sorting system 200 is shown in FIG. 2. Like and similar features are indicated with like reference numerals. As with the example shown in FIG. 1, the sorting system 200 is arranged to sort material according to at least one characteristic using the electrical capacitance of items in the material.

The example sorting system 200 is also described herein in relation to separation of variably differentiated stem cells, although it will be understood that other cell types and other particles having capacitance amounts at least partially dependent on a characteristic desired to form the basis of sorting are envisaged.

The sorting system 200 includes a cell delivery device 110 in this example of similar configuration and having similar components as the sorting system shown in FIG. 1. As such, during use charged droplets are produced by the cell delivery device 110 with at least some of the droplets including a respective cell and the droplets moving along a flowpath C.

The sorting system 200 includes an alternative deflection device 204 arranged to produce a magnetic field 210 extending in a direction substantially perpendicular to the flowpath C and perpendicular to the desired deflection direction. In this example, an electromagnet 212 is used to generate the magnetic field 210, although it will be understood that other devices suitable for generating a magnetic field are envisaged.

Several types of droplets may exit the collimator 124 and in this example the droplets include uncharged droplets 128 that for any reason have not acquired a charge, droplets 130 that have acquired a charge but do not include a cell, droplets 132 that have acquired a charge and that carry a respective first cell type, and droplets 134 that have acquired a charge and that carry a respective second cell type. In this example, the second cell type is more differentiated than the first cell type and, accordingly, the capacitance of the second cell type and therefore the charge acquired by the second cell type will be higher than the corresponding capacitance and charge acquired by the first cell type. Droplets 130 without cells, that is droplets substantially entirely made up of sheath fluid, have a higher associated capacitance than droplets with cells and, accordingly, acquire a higher charge than the droplets 132, 134 with cells.

The charged droplets 130, 132, 134 passing through the magnetic field 210 experience a force in a direction substantially perpendicular to both the flowpath C and the magnetic field 210 that is dependent on the amount of charge acquired by the droplets.

As with the example shown in FIG. 1, the droplets that have been caused to deviate from the flowpath C by the deflection device 204 are collected in first, second and third collection receptacles 140, 142, 144 respectively. The uncharged droplets 128 do not deviate from the flowpath C and continue to move along the flowpath C are received in a recycle tube 146.

The charge on each droplet q is calculated by:

$$q = V_c C \quad (1)$$

where $V_c$ is the charging voltage across the charging plates and C is the capacitance of the droplet.

The force on each droplet while passing through the magnetic field is given by $$F = qvB \quad (2)$$

where B is the magnetic field produced by the deflection device, v is the velocity of each droplet and q is the charge on each droplet.

The deflection force F causes an acceleration a in a transverse direction perpendicular to both the flowpath C and the magnetic field B, where:

$$F = ma \quad (3)$$

and substituting (1) and (2) into (3) gives the acceleration as:

$$a = V_c C_v B/m \quad (4)$$

Assuming that the droplet is travelling uniformly along the flowpath C at a velocity v prior to the deflection by the magnetic field B, after a distance x the deflection y is given by:

$$x = vt \text{ and } y = \frac{1}{2}at^2 \quad (5)$$

and by eliminating t, we get:

$$y = \frac{1}{2}a\frac{x^2}{v^2} \quad (6)$$

Substituting (4) into (6) we get that the deflection y is given by:

$$y = (V_c C B x^2)/(2mv) \quad (7)$$

which represents a parabolic path for the droplet where the deflection is proportional to the capacitance of the 2.5 droplet.

In equation (7), C represents the capacitance of the droplet, that is, $C_d$, and the deflection y in (7) can be written as:

$$y = V_c B/(2mv) \cdot C_s C_c/(C_s + C_c) \cdot x^2 \quad (8)$$

where $C_s$ is the capacitance of the sheath fluid around the cell and $C_c$ is the capacitance of the cell.

In a particular example, for deflection voltage $V_d=8000V$, magnetic field B=0.2 tesla acting over a distance of 10 cm, cells of diameter 10 microns surrounded by a 1 micron sheath of aqueous medium, droplet mass m=10-12 Kg, and velocity of cells=10 m/sec, the deflection is of the order of 9.2 mm for undifferentiated cells, 18.2 mm for differentiated cells and 35.6 mm for droplets without cells.

As with the example sorting system 100 shown in FIG. 1, there is considerable scope for tuning the system to provide optimal separation and high yield by varying the magnitude of the charging voltage and the deflecting magnetic field, by extending the range over which the magnetic field acts, varying the velocity of the droplets and the geometry of the plates and the positioning of the collecting receptacles 140, 142, 144.

For both examples described above, variations in cell or particle attributes can be accommodated by modifying the sizes and/or physical characteristics of the system components. For example, an increase in cell or particle diameter would be accommodated by a larger size collimator 124. Similarly, the location, size, and number of the collection receptacles and the deflection voltage can be adjusted to match the capacitance range of the sample.

The throughput is determined by the speed of the droplet generation process, which is in turn dependent on the sheath fluid pressure, the size of the nozzle, and the frequency of oscillation imparted by the separation device 126 and cell density of the sample. An approximate calculation of the throughput can be obtained as follows:

$$f = \frac{v}{4.5d} \quad (12)$$

where v is the velocity of the cell/sheath fluid and d is the diameter of the orifice of the collimator 124.

For a cell size of approx 10 micron diameter, a nozzle diameter of 50 microns, and a fluid velocity of 10 m/sec, the throughput in drops per sec is 44,000. However, not all drops will contain a cell and thus for a concentration of 1 in 5 we get a throughput of approx 8,000 cells sorted per second.

It will be appreciated that in order to increase throughput, several droplet streams may be provided in parallel. With this arrangement, several cell delivery devices 110 may be provided together with one, the same number, or a smaller number of deflection devices 114 than cell delivery devices 110.

With 10 nozzles in parallel the throughput could be increased to 80,000 per second, an order of magnitude larger than current sorting system known hitherto.

It will be understood that the deflection is reasonably insensitive to variations in cell radius and to the size of the sheath fluid shell.

Table 1 shows the impact on the deflection of a 20% fluctuation in each of these variables:

| Type of change | % Change | % Impact on Deflection |
| --- | --- | --- |
| Increase in capacitance of undifferentiated cell | 20 | 19 |
| Decrease capacitance of differentiated cell | −20 | −19 |
| Increase in cell size and in shell of surrounding water | 20 | 1 |

Figure 3:
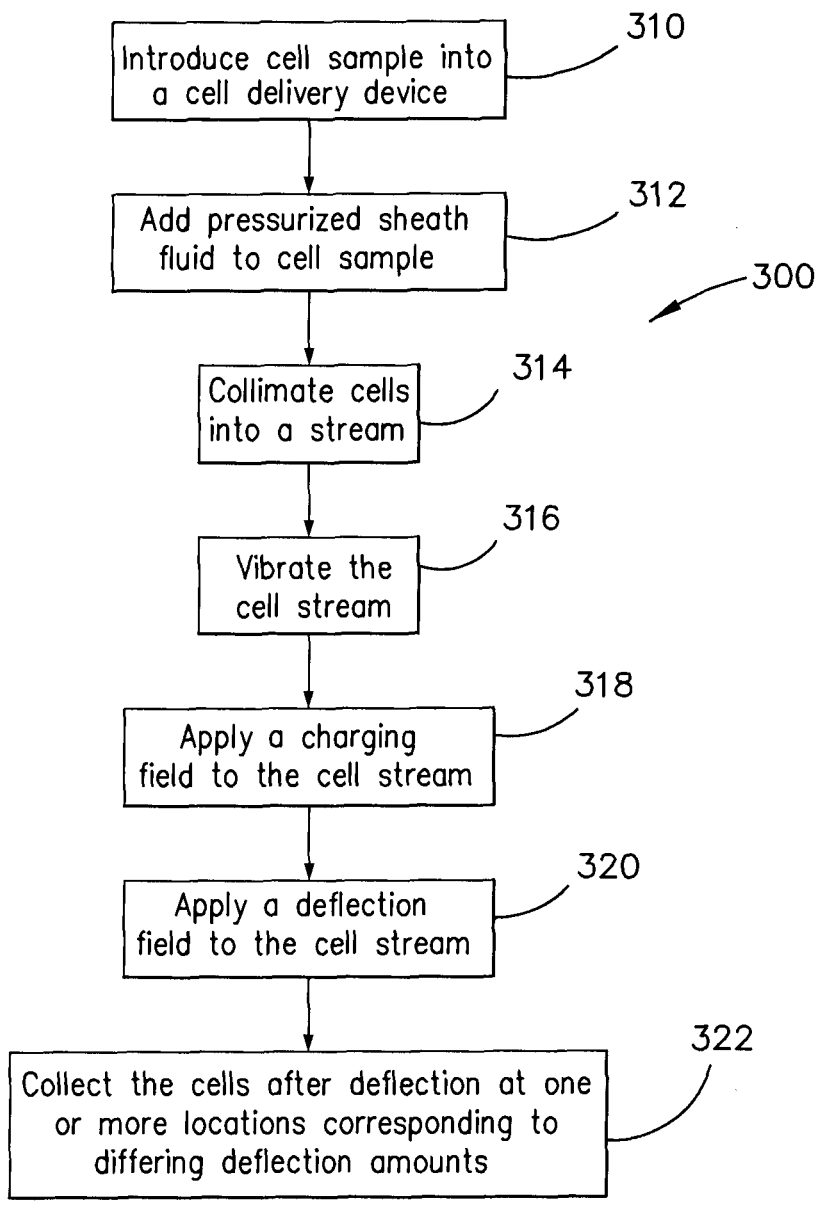
FIG. 3 is a flow diagram illustrating an example of a method of sorting cells.

An example method of sorting material using a sorting device of the type discussed above is shown in the flow diagram 300 in FIG. 3. In this example, the method is described in relation to sorting cells, in particular variably differentiated cells, although it will be understood that the method may be applied to sort any material wherein at least some particles or cells in the material have different associated capacitances.

The method 300 includes introducing 310 material to be sorted, in this example variably differentiated cells, into the cell delivery device 110, adding 312 pressurized sheath fluid to the material, and collimating 314 the mixture into a stream moving along a flowpath C. The stream is then separated so as to produce droplets containing cells, in this example by vibrating 316 the cell delivery device by applying a current to a piezo-electric device, and a charge is applied 318 to the cell droplets, in this example by applying a DC voltage to spaced charging plates. The droplet stream is then passed though a deflection device, in this example arranged to produce an electric or magnetic field 320 which causes each charged droplet to deviate from the flowpath C according to the amount of charge on the droplet. The variably deviated droplets are then collected 322 et several locations corresponding to the deviation amounts.

It will be appreciated that unlike the FACS method, with the present sorting system the cells do not need to be tagged, for example by a fluorescent marker.

It will also be appreciated that the present system and method is non-invasive in that there is no need to pre-treat cells and potentially damage them. Some consequences may include but are not limited to one or more of, yield may be improved, higher speeds may be achieved, and less cost may be involved than sorting methods and systems such as those associated with FACS type devices.

Furthermore, it will be appreciated that the present system and method may be used to isolate particular cells or particles from a sample, for example cells at a particular level of differentiation by collecting cells at a location corresponding to deviation of the particular cells.

It will also be understood that the present system and method may also be used to measure capacitance of cells or particles. For example, by appropriately calibrating the system, the deviation location of the cells or particles may be used as a measure of the charge imparted to the cells or particles and thereby the capacitance of the cells or particles. In this way, the system can operate as a capacitance measurement system.

Modifications and variations as would be apparent to a skilled addressee are deemed to be within the scope of the present invention.

The invention claimed is:

1. A cell sorting system for isolating target cells having at least one cell characteristic associated with a target cell capacitance from a sample of cells, the system comprising:
    an electrical charge device arranged to produce electrical charging conditions for substantially all cells of a sample of cells such that an electrical charge at least partially dependent on cell capacitance is imparted to one or more cells of the sample of cells;
    a cell delivery device operably connected to the electrical charge device and arranged to cause the one or more cells to move along a flowpath;
    a deflection device arranged to cause the one or more cells to deviate from the flowpath an amount at least partially dependent on the electrical charge imparted to the cell;
    a collection device in fluid communication with the deflection device, the collection device arranged to collect one or more target cells having at least one target cell capacitance at a location corresponding to the amount of deviation of the target cells from the flowpath; and
    a recycle device arranged along the flowpath to return to the electrical charge device cells that have not been caused to deviate from the flowpath.

2. A system as claimed in claim 1, wherein the electrical charge device comprises a first DC electric field generator.

3. A system as claimed in claim 1, wherein the electrical charge device comprises an electro-spray charging device.

4. A system as claimed in claim 1, wherein the electrical charge device comprises an aerosolization charging device.

5. A system as claimed in claim 1, wherein the charging conditions are substantially the same for all cells of the sample.

6. A system as claimed in claim 1, wherein the deflection device comprises a second DC electric field generator arranged to generate an electric field crossing a path of movement of the cells.

7. A system as claimed in claim 6, wherein the second DC electric field generator comprises at least 2 charged deflection plates.

8. A system as claimed in claim 1, wherein the deflection device comprises a magnetic field generator arranged to generate a magnetic field crossing a path of movement of the cells.

9. A system as claimed in claim 8, wherein the magnetic field generator comprises an electro-magnet.

10. A system as claimed in claim 1, wherein the cell delivery device comprises a cell separation device arranged to cause substantially all of the cells to separate from each other.

11. A system as claimed in claim 10, wherein the cell separation device comprises a vibration device arranged to cause substantially all of the cells to vibrate.

12. A system as claimed in claim 1, wherein the cell delivery device comprises a collimator arranged to collimate the cells.

13. A system as claimed in claim 12, wherein the cell delivery device comprises a sheath fluid input for communicating sheath fluid to cells disposed in the cell delivery device.

14. A system as claimed in claim 1, comprising a plurality of collection receptacles arranged to collect cells at a plurality of locations corresponding to different deflection amounts.

15. A system as claimed in claim 1, comprising a plurality of cell delivery devices.

16. A method of isolating target cells having at least one cell characteristic associated with a target cell capacitance from a sample of cells, the method comprising:
  providing a sample of cells;
  producing electrical charging conditions for substantially all cells of the sample of cells such that an electrical charge at least partially dependent on cell capacitance is imparted to one or more cells of the sample of cells;
  causing the cells to move along a flowpath;
  causing the cells to deviate from the flowpath an amount at least partially dependent on the electrical charge imparted to the cell;
  collecting the target cells having the at least one target cell capacitance at a location corresponding to the amount of deviation of the target cells from the flowpath; and
  recycling cells that have not been caused to deviate from the flowpath such that the recycled cells are re-subjected to the electrical charge.

17. A method as claimed in claim 16, wherein the electrical charging conditions are produced by producing a first DC electric field.

18. A method as claimed in claim 16, wherein the electrical charging conditions are produced using an electro-spray charging device.

19. A method as claimed in claim 16, wherein the electrical charging conditions are produced using an aerosolization charging device.

20. A method as claimed in claim 16, comprising producing charging conditions that are substantially the same for all cells in the sample.

21. A method as claimed in claim 16, wherein the step of causing the one or more cells to deviate from the flowpath comprises producing a second DC electric field crossing the flowpath.

22. A method as claimed in claim 21, comprising producing the second DC electric field using at least 2 charged deflection plates.

23. A method as claimed in claim 16, wherein the step of causing the one or more cells to deviate from the flowpath comprises producing a magnetic field crossing the flowpath.

24. A method as claimed in claim 23, comprising producing the magnetic field using an electro-magnet.

25. A method as claimed in claim 16, comprising causing substantially all of the cells to separate from each other.

26. A method as claimed in claim 25, comprising causing substantially all of the cells to vibrate so that the cells are caused to separate.

27. A method as claimed in claim 16, comprising collimating the cells.

28. A method as claimed in claim 27, comprising supplying sheath fluid to cells disposed in the cell delivery device.

29. A method as claimed in claim 16, comprising producing a plurality of cell flowpaths, and causing the cells to move along respective flowpaths.

30. A method of isolating target cells as claimed in claim 16, wherein the target cells are differentiated cells.

31. A method of measuring capacitance of one or more particles, the method comprising:
  providing one or more particles;
  producing electrical charging conditions for the one or more particles such that an electrical charge at least partially dependent on capacitance of the one or more particles is imparted to the one or more particles;
  causing the one or more particles to move along a flowpath;
  causing each particle to deviate from the flowpath an amount at least partially dependent on the electrical charge imparted to the particle;
  collecting one or more particles at one or more locations corresponding to the amount of deviation of the one or more particles from the flowpath, each of the one or more locations corresponding to a capacitance amount; and
  causing particles that have not deviated from the flowpath to be re-subjected to the electrical charge.

\* \* \* \* \*

UNITED STATES PATENT AND TRADEMARK OFFICE
CERTIFICATE OF CORRECTION

| | | |
|---|---|---|
| PATENT NO. | : 9,267,873 B2 | Page 1 of 1 |
| APPLICATION NO. | : 13/376544 | |
| DATED | : February 23, 2016 | |
| INVENTOR(S) | : Kery et al. | |

It is certified that error appears in the above-identified patent and that said Letters Patent is hereby corrected as shown below:

In the Specification

In Column 1, Line 8, delete "§371" and insert -- § 371 --, therefor.

In Column 3, Line 54, delete "froth the" and insert -- from the --, therefor.

In Column 8, Line 43, delete "of the 2.5" and insert -- of the --, therefor.

In Column 10, Line 2, delete "322 et" and insert -- 322 at --, therefor.

Signed and Sealed this
Twenty-fourth Day of May, 2016

Michelle K. Lee
*Director of the United States Patent and Trademark Office*